United States Patent

Chevallet et al.

Patent Number: 6,039,877
Date of Patent: Mar. 21, 2000

[54] DEVICE AND METHOD FOR PREPARING A TREATMENT LIQUID BY FILTRATION

[75] Inventors: Jacques Chevallet, Serezin Du Rhone; Jean-Claude Riquier, Rillieux, both of France

[73] Assignee: Hospal Industrie, Meyzieu, France

[21] Appl. No.: 08/934,903

[22] Filed: Sep. 22, 1997

Related U.S. Application Data

[62] Division of application No. 08/462,435, Jun. 5, 1995, Pat. No. 5,702,597.

[30] Foreign Application Priority Data

Jul. 26, 1994 [FR] France ................................. 94-09499

[51] Int. Cl.[7] .................................................. B01D 61/00
[52] U.S. Cl. .............................. 210/636; 210/90; 210/97; 210/111; 210/134
[58] Field of Search ................. 210/636, 195.2, 210/791, 90, 111, 97, 134

[56] References Cited

U.S. PATENT DOCUMENTS

| | | | |
|---|---|---|---|
| 3,956,114 | 5/1976 | Del Pico et al. | 210/636 |
| 4,191,182 | 3/1980 | Popovich et al. . | |
| 4,206,055 | 6/1980 | Hauk et al. . | |
| 4,606,826 | 8/1986 | Sano et al. . | |
| 4,680,122 | 7/1987 | Barone . | |
| 4,702,829 | 10/1987 | Polaschegg et al. . | |
| 4,834,888 | 5/1989 | Polaschegg . | |
| 4,921,610 | 5/1990 | Ford et al. | 210/636 |
| 4,931,186 | 6/1990 | Ford et al. . | |
| 5,066,402 | 11/1991 | Anselme et al. . | |
| 5,112,489 | 5/1992 | Hartmann | 210/637 |
| 5,178,763 | 1/1993 | Delaunay . | |
| 5,431,811 | 7/1995 | Tusini et al. . | |
| 5,476,592 | 12/1995 | Simard . | |
| 5,693,229 | 12/1997 | Hartmann | 210/195.2 |
| 5,702,597 | 12/1997 | Chevallet et al. | 210/195.2 |

FOREIGN PATENT DOCUMENTS

| | | |
|---|---|---|
| 0 121 085 A1 | 10/1984 | European Pat. Off. . |
| 0 479 492 A1 | 4/1992 | European Pat. Off. . |
| 0 570 349 A1 | 11/1993 | European Pat. Off. . |
| 0 571 303 A1 | 11/1993 | European Pat. Off. . |
| 2 135 598 | 9/1984 | United Kingdom . |

OTHER PUBLICATIONS

Derwent Abstract 84–296090/48, EP126714A, Nov. 28, 1984.

*Primary Examiner*—Ana Fortuna
*Attorney, Agent, or Firm*—Finnegan, Henderson, Farabow, Garrett & Dunner, L.L.P.

[57] ABSTRACT

A device for treatment of blood by extracorporeal circulation comprises a dialysis liquid circuit having a supply tube (9a, 9b) on which is arranged a filter (21) having a first chamber and a second chamber (22, 23) which are separated by a filtering membrane (24), the supply tube having a first portion (9a) connecting a dialysis liquid source (10) to an inlet of the first chamber (22), and a second portion (9b) having an end connected to an outlet of the second chamber (23) of the filter (21) and another end which can be connected to an inlet of a compartment (3) of an exchanger (1) with semipermeable membrane (4). A feedback tube (25) connects the inlet of the first chamber (22) of the filter (21) to the outlet of the first chamber (22). A flushing pump (26) is arranged on the feedback tube (25) for circulating liquid in the first chamber (22) of the filter (21) and causing cleaning of the membrane (24) by tangential flushing.

8 Claims, 2 Drawing Sheets

DEVICE AND METHOD FOR PREPARING A TREATMENT LIQUID BY FILTRATION

This is a division of application Ser. No. 08/462,435, filed Jun. 5, 1995, now U.S. Pat. No. 5,702,597.

BACKGROUND OF THE INVENTION

1. Field of the Invention

The subject of the present invention is a device for treatment of blood by extracorporeal circulation, designed to produce a sterile and pyrogen free treatment liquid.

2. Description of the Related Art

Patients suffering from renal insufficiency may undergo various treatments involving extracorporeal circulation of blood, haemodialysis, haemofiltration and haemodiafiltration.

Haemodialysis consists in circulating the blood of the patient in a first compartment of a dialyser, and a dialysis liquid in a second compartment of the dialyser, the two compartments being separated by a semipermeable membrane allowing diffusive transfer of solutes through the membrane, from the compartment in which the concentration of a particular solute is the highest to the compartment in which the concentration of this solute is the lowest.

Haemofiltration consists in extracting a fraction of plasmatic water or filtrate from the blood of the patient by means of a haemofilter and in simultaneously infusing into the patient a substitution liquid in order to compensate, in general only partially, for the quantity of filtrate extracted.

Haemodiafiltration is a combination of the two aforementioned treatments.

The dialysis liquid and the substitution liquid are liquids which have substantially the same composition. They are isotonic with the blood of which they contain the main electrolytes.

In conventional dialysis machines, the dialysis liquid is prepared by mixing water and concentrated solutions or pulverulent salts comprising the main electrolytes of blood. This dialysis liquid is neither sterile nor pyrogen free, that is to say that it may contain living microorganisms (bacteria) as well as components called pyrogens, the introduction of which into the body may produce undesirable effects, such as fever, shivering, nausea or anaphylactoid reactions.

Although the membrane of the dialyser isolates the blood from the dialysis liquid and, during treatment, a positive transmembrane pressure is set up between the blood compartment and the dialysis-liquid compartment of the dialyser in order to prevent the passage of dialysis liquid into the blood, not all contamination of the blood by bacteria and pyrogenic components contained in the dialysis liquid is completely excluded, especially in the event of breakage of the filter or in the event of accidental reversal of the direction of the transmembrane pressure when a dialyser with high hydraulic permeability is used.

Repeated interest in the use of sterile and pyrogen free dialysis liquid has moreover been expressed. It has, in particular, been proposed to filter the dialysis liquid in a filter having a first chamber and a second chamber which are separated by a membrane having a high hydraulic permeability, the first chamber having an inlet for introducing the liquid to be filtered and an outlet for discharging the substances trapped by the membrane together with a fraction of the liquid introduced into the filter (see "Investigation of the Permeability of Highly Permeable Polysulfone Membranes for Pyrogens" in Contr. Nephrol., vol. 46, pp. 174–183, Karger, Basel 1985).

European Patent 0,270,794 describes a dialysis machine whose dialysis liquid circuit comprises:

a supply tube on which is arranged a filter having a first chamber and a second chamber which are separated by a filtering membrane, the supply tube having a first portion connecting a dialysis liquid source to an inlet of the first chamber, and a second portion having an end connected to an outlet of the second chamber of the filter and another end which can be connected to an inlet of a first compartment of a dialyser;

a discharge tube having an end which can be connected to an outlet of the first compartment of the dialyser; and a purge tube on which a valve is arranged connecting an outlet of the first chamber of the filter to the discharge tube.

During operation, the valve arranged on the purge tube is opened at regular time intervals in order to purge the first chamber of the filter of the microorganisms and pyrogenic components trapped by the membrane.

This machine has several drawbacks. In particular, it is clear that the valve of the purge tube cannot be opened frequently because of the interruption to the treatment which results therefrom. (As a matter of fact, because of the significant head loss which the membrane of the filter constitutes, when the valve is opened, any dialysis liquid coming from the dialysis liquid source flows through the purge tube and the dialyser is no longer supplied with fresh dialysis fluid). Furthermore, between two successive openings of the valve, there is a time lag during which the undesirable substances accumulate in the first chamber of the filter where they tend to be entrained by convection towards the membrane and to clog it. The result of this is, in the event of breakage of the membrane of the filter, that these accumulated substances are sent into the dialyser and the dialysis circuit portion located upstream and downstream thereof, which these substances contaminate. Also, the tangential flushing of the membrane which results from intermittent opening of the valve cannot be sufficiently long to detach from the membrane all the substances which have adhered thereto.

SUMMARY OF THE INVENTION

One object of the invention is to produce a dialysis/haemofiltration machine capable of producing a treatment liquid (dialysis liquid, substitution liquid) which is made sterile and pyrogen free by filtration, in which the cleaning of the filter used causes little or no interruption to the treatment being carried out and makes it possible to optimize the working life of the filter.

In order to achieve this object, a device for treatment of blood by extracorporeal circulation is provided, according to the invention, comprising a dialysis liquid circuit having:

a supply tube on which is arranged a filter having a first chamber and a second chamber which are separated by a filtering membrane, the supply tube having a first portion connecting a dialysis liquid source to an inlet of the first chamber, and a second portion having an end connected to an outlet of the second chamber of the filter and another end which can be connected to an inlet of a compartment of an exchanger with semipermeable membrane;

a discharge tube having an end which can be connected to an outlet of the compartment of the exchanger; and a purge tube on which a flow-control element (for example a valve) is arranged and which is connected to an outlet of the first chamber of the filter, characterized in that it comprises a feedback tube connecting the inlet of the first chamber of the filter to the outlet of the first chamber, and on which is arranged a flushing pump for circulating liquid in the first chamber of the filter and causing cleaning of the membrane by tangential flushing.

By virtue of this arrangement, the cleaning of the membrane by tangential flushing is optimal, on the one hand, because this flushing is continuous and, on the other hand, because, being independent of the circulation rate of the dialysis liquid in the dialysis liquid circuit, it can be adjusted (by setting the flushing pump) so as to be as efficient as possible. The working life of the filter is directly linked with the efficiency of the cleaning to which it is subjected.

According to one characteristic of the invention, the device comprises means for detecting clogging of the membrane of the filter and control means for controlling the flow-control element of the discharge tube as a function of a predetermined clogging threshold of the membrane so as to cause purging of the first chamber of the filter.

By virtue of this arrangement, the frequency of the purges of the first chamber of the filter only depends on the bacteria and pyrogens content of the dialysis liquid to be filtrated so that, if the water used for preparing the dialysis liquid is very clean, the valve of the purge tube is not open or only once or twice per treatment session.

According to another characteristic of the invention, the device comprises means for calculating the frequency of the purges and comparing the calculated frequency with a reference frequency; the control means are then designed to increase the flow rate of the flushing pump when the calculated frequency of the purges reaches the reference frequency.

In this way, the intensity of the cleaning of the filter can be adjusted as a function of the rate at which it clogs up, that is to say also as a function of the degree of purity of the dialysis liquid coming from the dialysis liquid source.

According to yet another characteristic of the invention, the device includes means for storing in memory an initial transmembrane pressure when the filter is set in operation for the first time and means for comparing the initial transmembrane pressure with the transmembrane pressure measured. The device may furthermore include alarm means for emitting an alarm when the transmembrane pressure measured deviates by a predetermined quantity from the initial transmembrane pressure.

It has been observed that, with equal dialysis liquid flow rate in the dialysis liquid circuit, the transmembrane pressure in the filter increases over time, so that the comparison between the transmembrane pressure when the filter is set in operation and the transmembrane pressure measured at a given instant in the use of the filter gives an accurate idea of the ageing of the filter. It is therefore possible to define an optimal individual working life for each filter, corresponding to a relative increase in the transmembrane pressure.

According to yet another characteristic of the invention, the device includes means, such as a flow meter, for monitoring a quantity of dialysis liquid, which means are arranged on the supply tube, and the filter is placed on the supply tube between the dialysis liquid source and the means for monitoring a quantity of dialysis liquid.

This arrangement has several advantages: first, a filtered liquid passes through the monitoring means, which is entirely suitable when these means consist of a flow meter, and in particular a turbine or gear flow meter whose operation may be seriously disturbed by a solid impurity and is generally degraded by progressive fouling. Furthermore, such monitoring means may form part of a volumetric ultrafiltration control system by means of which, in a portion of the dialysis liquid circuit comprising the exchanger, the quantity of dialysis liquid leaving this circuit portion is kept equal to the quantity of dialysis liquid which enters it. Second means for monitoring the quantity of dialysis liquid are then arranged on the discharge tube of the dialysis liquid circuit. By connecting the filter to the dialysis liquid circuit outside the portion of the dialysis liquid circuit in which a constant volume of liquid circulates, the necessity of having to connect the purge tube to the discharge tube of the dialysis circuit upstream of the second monitoring means is avoided, that is to say also of having to introduce therein the impurities trapped by the filter as is the case in the device described in European Patent 0,270,794 mentioned hereinabove. Yet another advantage of this arrangement is that the purge tube can be directly connected to the drain by an outlet channel of the dialysis machine which is independent of the outlet channel by which the spent-liquid discharge tube is connected to the drain. In this way, the portion of the dialysis liquid circuit which is located upstream of the filter is completely isolated by the filter from the dialysis liquid circuit portion located downstream of the filter. Contamination of the discharge tube, both downstream and upstream (back-contamination) of the junction of the purge tube with the discharge tube, which occurs on the device described in the prior art, is therefore completely avoided.

A further subject of the invention is a method for cleaning a filter having two chambers separated by a filtering membrane, a first chamber being connected to a treatment liquid source, a second chamber having an outlet for the filtered treatment liquid, characterized in that it consists in continuously recirculating treatment liquid into the first chamber in order to cause tangential flushing of the membrane of the filter and to prevent clogging of the membrane by the substances stopped by the membrane.

According to one characteristic of the invention, the method furthermore comprises the steps of:
  measuring a clogging level of the filter;
  comparing the clogging level measured with a predetermined clogging threshold; and
  purging the first chamber of the filter when the clogging level measured reaches the predetermined clogging level.

According to another characteristic of the invention, the method furthermore consists in comparing the actual frequency of the purges of the first chamber of the filter with a reference frequency and in increasing the rate of recirculation into the first chamber of the filter when the actual frequency reaches the reference frequency.

The method may be particularly adapted to a filter arranged in a volumetric ultrafiltration control system of a haemodialysis/haemofiltration machine, the ultrafiltration control system comprising two elements for monitoring a quantity of liquid, such as two flow meters, arranged on a dialysis liquid circuit respectively upstream and downstream of a haemodialyser, the two flow meters being directly connected in series in repetitive fashion by a branch line to the haemodialyser in order to be subjected to calibration. In this arrangement, according to yet another characteristic of the invention, purging of the first chamber of the filter is ordered during calibration of the flow meters following the instant when the clogging level measured reaches the predetermined clogging threshold.

A further subject of the invention is a method for determining the ageing of a filter having two chambers separated by a filtering membrane, a first chamber being connected to a treatment liquid source and a second chamber having an outlet for the filtered treatment liquid, characterized in that it comprises the steps of:

measuring and storing in memory, for a given treatment liquid flow rate, a reference transmembrane pressure in the filter the first time the filter is set in operation;

measuring, on each subsequent use of the filter, the transmembrane pressure at the given treatment liquid flow rate;

comparing the transmembrane pressure measured with the reference transmembrane pressure.

Other characteristics and advantages of the invention will emerge on reading the following description.

BRIEF DESCRIPTION OF THE DRAWINGS

Reference will be made to the attached drawings, in which.

DESCRIPTION OF THE PREFERRED EMBODIMENTS

Figure 1:
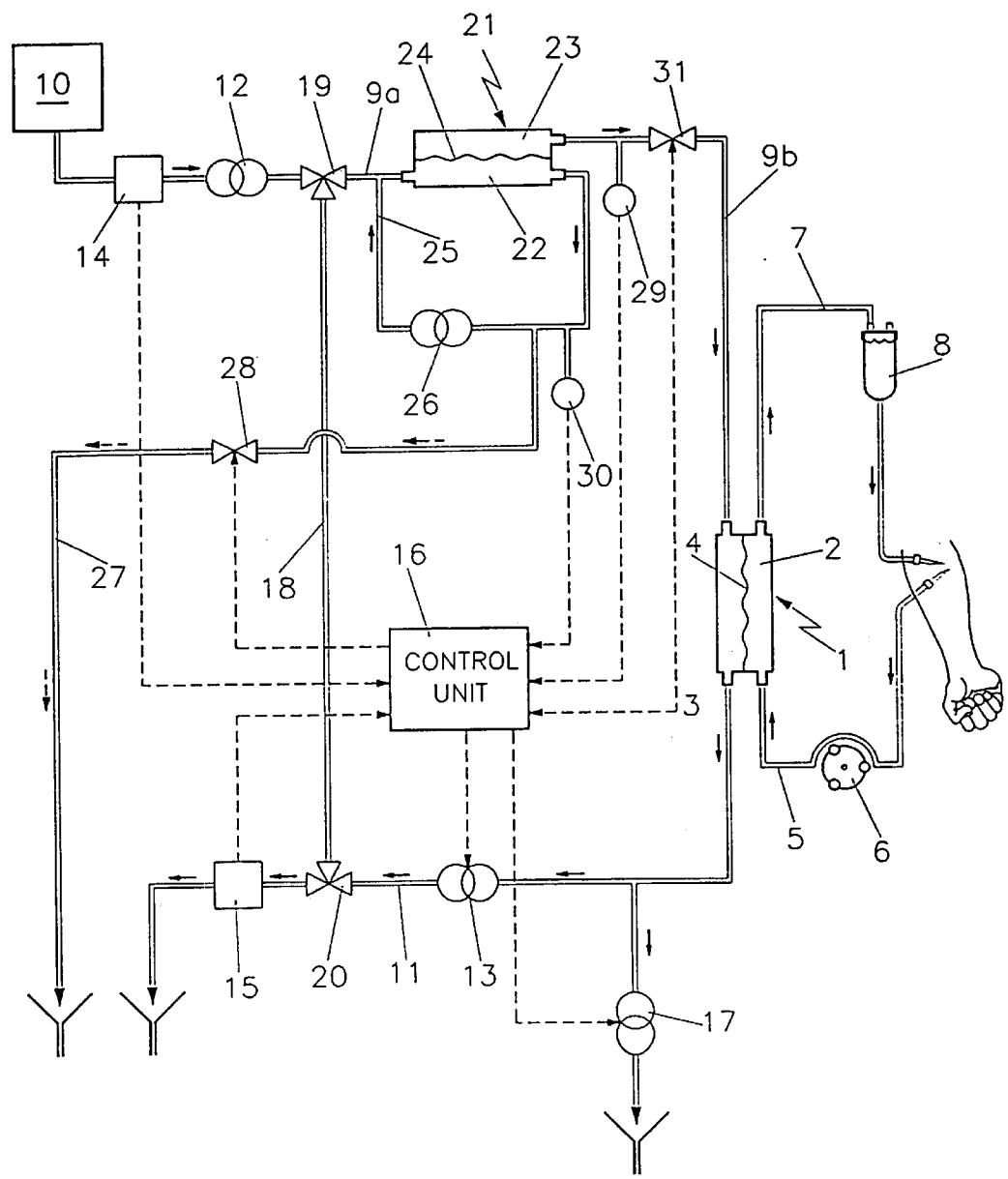
FIG. 1 is a diagram of a dialysis device comprising a dialysis-liquid filtration system according to the invention.

The device for treatment of blood by extracorporeal circulation represented in FIG. 1 is suitable for carrying out a dialysis treatment. This device comprises a haemodialyser 1 having two compartments 2, 3 which are separated by a semipermeable membrane 4, a first compartment 2 being connected to an extracorporeal blood circulation circuit, a second compartment 3 being connected to a dialysis liquid circulation circuit. In conventional manner, all the components of the device which will be described hereinbelow, with the exception of the blood circulation circuit and the haemodialyser, are arranged within a so-called dialysis machine.

The blood circulation circuit comprises a withdrawal tube 5 connected to an inlet of the first compartment 2, on which tube a pump 6 is arranged, and a delivery tube 7 connected to an outlet of the first compartment 2, on which tube a bubble trap 8 is mounted.

The dialysis liquid circuit comprises a supply tube (9a, 9b) for fresh dialysis liquid, connecting a dialysis liquid source 10 to an inlet of the second compartment 3 of the haemodialyser 1, and a discharge tube 11 for spent liquid, connecting an outlet of the second compartment 3 of the haemodialyser 1 to the drain.

The dialysis liquid source is, for example, a dialysis liquid generator 10 using which water is heated, degassed then mixed, in determined proportions, with concentrated solutions containing the main electrolytes of blood. The dialysis liquid produced is neither sterile nor pyrogen free.

The dialysis liquid circuit comprises dialysis liquid circulation means consisting of a first pump 12 arranged on the supply tube (9a, 9b) and a second pump 13 arranged on the discharge tube 11.

The device also comprises a volumetric ultrafiltration control system comprising a first means for monitoring a quantity of dialysis liquid, such as a first flow meter 14, arranged on the supply tube (9a, 9b,) and a second means for monitoring a quantity of dialysis liquid, such as a second flow meter 15, arranged on the discharge tube 11 downstream of the second circulation pump 13. The measurements taken by the two flow meters are compared by a calculation and control unit 16 which drives the second dialysis liquid circulation pump 13 so that the flow rates measured by the two flow meters are identical. The ultrafiltration control system furthermore comprises an ultrafiltration pump 17 connected to the discharge tube upstream of the second pump 13. By virtue of the above-described slaving of the second pump 13, the quantity of liquid extracted from the dialysis liquid circuit by the ultrafiltration pump 17 corresponds exactly to the quantity of plasmatic water which passes from the blood into the dialysis liquid by ultrafiltration through the membrane 4 under the effect of the relative pressure reduction created in the dialysis liquid circuit by the ultrafiltration pump 17. A branch tube 18 connects the supply tube (9a, 9b) to the discharge tube 11, to which tubes it is connected, via two three-way valves 19, 20, respectively downstream of the first flow meter 14 and upstream of the second flow meter 15. This branch line 18 makes it possible to arrange the flow meters 14, 15 directly in series for programmed calibration at regular intervals.

The device furthermore comprises a filter 21 for filtering the dialysis liquid produced by the dialysis liquid generator 10. The filter 21 has a first chamber and a second chamber 22, 23 which are separated by a filtering membrane 24, the first chamber 22 having an inlet connected to a first portion 9a of the supply tube and the second chamber 23 having an outlet connected to a second portion 9b of the supply tube, on which a valve 31 is arranged.

According to the invention, a feedback tube 25, on which a flushing pump 26 is arranged, connects an outlet of the first chamber 22 of the filter 21 to the inlet of this first chamber. A tube 27 for purging the first chamber 22 of the filter 21, on which tube a flow-control element such as a valve 28 is arranged, is connected to the feedback tube 25 between the outlet of the first chamber 22 of the filter 21 and the pump 26. The purge tube 27 is connected to the drain by an outlet of the dialysis machine which is separate from the outlet which forms the end of the discharge tube 11 for the spent liquid.

Two pressure sensors 29, 30 are arranged, respectively, on the second portion 9b of the supply tube and on the feedback tube 25, at the outlet of the first and second chambers 22, 23 of the filter 21, in order to measure the pressure in these chambers. The information delivered by the pressure sensors 29, 30 is supplied to the control and calculation unit 16 which can calculate the transmembrane pressure in the filter 21 and control the operation of the device as a function of the measured and calculated values of the pressures in the filter 21, as will be explained hereinbelow.

When the steps preliminary to the treatment have been completed, that is to say the initial rinsing and filling of the dialysis liquid circuit 9a, 9b, 11, of the haemodialyser 1 and of the blood circuit 5, 7, 8 and the connection of the blood circuit to the vascular circuit of the patient, the dialysis liquid produced by the dialysis liquid generator 10 is set in circulation in the dialysis liquid circuit by means of the pumps 12 and 13, and the blood of the patient is set in circulation in the blood circuit by means of the pump 6 (the valve 31 is then opened and the valves 19, 20 are arranged so as to allow circulation in the supply tube 9a, 9b and in the discharge tube 11).

Furthermore, the valve 28 of the purge tube 27 is closed and the flushing pump 26 rotates at a predetermined speed so that unfiltered liquid coming from the generator circulates continuously in the first chamber 22 of the filter 21 and flushes the membrane 24, which has the effect of opposing its clogging by keeping in suspension the impurities stopped by the membrane of the filter.

In a conventional manner, the flow meters 14 and 15 are calibrated at regular time intervals. During these successive calibrations, the valves 19 and 20 are arranged so that the dialysis liquid circulates in the branch tube 18, and the first circulation pump 12 and the ultrafiltration pump 17 rotate at their set-point value, whilst the second circulation pump 13 is stopped.

According to the invention, the purging of the first chamber 22 of the filter 21, intended to remove the impurities stopped by the membrane 24, is ordered when a predetermined clogging level of the membrane is detected. More precisely, the control unit 16 compares, either continuously or at regular time intervals, the instantaneous value of the transmembrane pressure in the filter 21, calculated on the basis of the information delivered by the pressure sensors 29, 30, with a reference value calculated at the start of the session. When the instantaneous value exceeds the reference value by a predetermined quantity, a purge of the first chamber 22 of the filter 21 is ordered during the subsequent calibration phase of the flow meters 14, 15. The valve 31 is then closed and the purge valve 28 is opened for the time necessary for discharging, via the purge tube 27, the liquid contained in the first chamber 22 of the filter 21 and in the feedback tube 25.

According to the invention, the frequency of the purges is calculated by the calculation unit and is compared with a reference frequency. If the frequency calculated reaches or exceeds the reference frequency, the speed of rotation of the pump 26 is increased so that the efficiency of the cleaning of the membrane by tangential flushing is enhanced.

According to the invention, the ageing of the filter 21 is measured by starting with the observation that, during time and despite the continuous cleaning to which the membrane 24 is subjected, the transmembrane pressure in the filter rises, for equal dialysis liquid flow rates. The control and calculation unit 16 therefore compares, at regular time intervals, a reference transmembrane pressure which corresponds, for example, to the transmembrane pressure of the filter calculated the first time it is set in operation for a fixed dialysis liquid flow rate, with the instantaneous transmembrane pressure measured with the same flow rate, and when the latter deviates from the former by a predetermined quantity, it emits an alarm or a message on a display unit (not shown) in order to signal to the user that the filter 21 should be changed.

Figure 2:
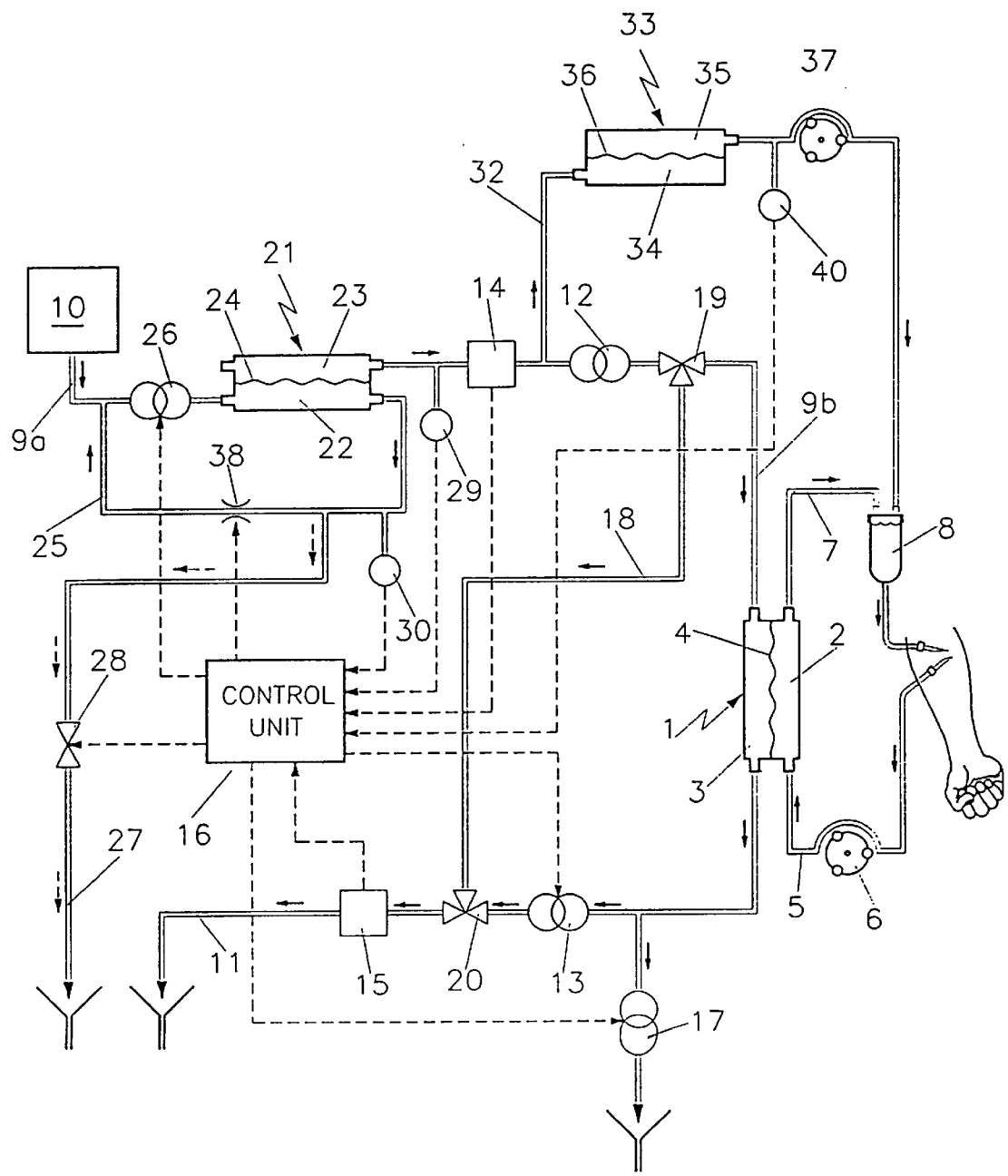
FIG. 2 is a diagram of a haemodiafiltration device comprising a treatment-liquid filtration system according to the invention.

FIG. 2 represents a haemodiafiltration device which differs from the haemodialysis device described hereinabove by the following characteristics (the components of these two devices which fulfill the same functions have been denoted by the same reference numbers).

In accordance with its purpose, this device includes means for infusing into the patient a substitution liquid intended to compensate, generally in part, for the quantity of plasmatic water withdrawn from the vascular circuit of the patient by ultrafiltration in the high-permeability haemodialyser 1. The infusion means comprise a substitution liquid tube 32 having a first portion connecting the dialysis-liquid supply tube 9a, 9b to an inlet of a first chamber 34 of a second filter 33, and a second portion connecting an outlet of a second chamber 35, separated from the first chamber 34 by a filtering membrane 36, to the bubble trap 8 of the extracorporeal blood circulation circuit. A substitution liquid circulation pump 37 is arranged on the second portion of the substitution liquid tube 32. The substitution liquid tube is connected to the supply tube 9a, 9b between the element 14 for measuring a quantity of dialysis liquid (for example flow meter) and the first dialysis liquid circulation pump 12.

In this device, the first filter 21 is not connected to the dialysis-liquid supply tube 9a, 9b inside the volumetric ultrafiltration control system (flow meters 14, 15, portion of the dialysis liquid circuit extending between the flow meters and the ultrafiltration pump 17) but outside this system, upstream of the first flow meter 14. As mentioned hereinabove, by virtue of this arrangement, the liquid circulating in the first flow meter 14 is a filtered liquid, which prevents fouling and, should the need arise, accidental blocking of this sensitive measurement element.

Another difference with the device represented in FIG. 1 is that the flushing pump 26 is arranged immediately upstream of the first chamber 22 of the first filter 21, on a tube portion common to the supply tube 9a and to the feedback tube 25. In operation, the flushing pump 26 is set to a flow rate greater than the sum of the flow rates of the circulation pump 12 and of the substitution liquid pump 37, so that a determined recirculation rate is set up in the feedback tube 25. A restricting element 38, which may optionally be adjustable, is arranged on the feedback tube 25, by virtue of which it is possible to obtain a sufficient pressure in the dialysis liquid circuit upstream of the circulation pump 12 for the pressure in the second chamber 35 of the second filter 33, as measured by a pressure sensor 40, to be always positive or at least zero, whatever the flow rate of the substitution liquid pump 37. The restriction element 38 may consist of a calibrated portion of the feedback tube 25.

The operation of this second device is as follows, in so far as it differs from that of the device represented in FIG. 1.

With the various pumps of the installation rotating at the rates prescribed by the operator or programmed by default or calculated, either at the start or during the session, the calculation and control unit 16 compares, either continuously or at regular time intervals, the pressure measured by means of the sensor 29 in the second chamber 23 of the filter 21 with a set-point pressure and it drives the flushing pump 26 so that the instantaneous pressure tends towards the set-point pressure. The set-point pressure is chosen so that the pressure in the second chamber 35 of the second filter 33, as measured by the pressure sensor 40, is always positive or at least zero, taking into account the substitution liquid flow rate imposed on the pump 37.

In order to measure the degree of clogging of the membrane of the filter 21, two methods are possible. Either, as described hereinabove, the transmembrane pressure in the filter 21 is calculated by virtue of the data supplied by the pressure sensors 29, 30 and is compared with a reference transmembrane pressure stored in memory (for example the transmembrane pressure measured at the start of the session). Or the speed of rotation of the flushing pump 26 is compared with a reference speed (for example the speed of rotation measured at the start of the session and stored in memory in the control unit 16). Since the pressure is kept constant in the second chamber 23 of the filter 21 by the regulating of the speed of rotation of the flushing pump 26, if the membrane 24 becomes clogged, the speed of rotation of the pump will be increased commensurately. When the measured value of the parameter in question (transmembrane pressure or speed of rotation of the flushing pump) reaches the corresponding reference value, the control unit 16 commands opening of the purge valve 28 for the time necessary to discharge the liquid contained in the first chamber 23 of the filter 21 and in the feedback tube 25.

The invention is not limited to the specific embodiments which have just been described, and it may comprise variants. In particular, although this variant may be considered to be less advantageous, the purge tube 27 of the device in FIG. 1 might be connected to the discharge tube 11 for spent liquid inside the volumetric ultrafiltration control system, that is to say upstream of the second means 15 for measuring a quantity of spent liquid.

Moreover, the flow control element 28 arranged on the purge tube 27 might consist of a pump. In the device in FIG. 2, this pump might rotate continuously so that the impurities trapped by the membrane are removed continuously as they collect.

We claim:

1. A method for cleaning a filter having a first chamber and a second chamber separated by a filtering membrane, the first chamber having an outlet and having an inlet connected to a treatment liquid source, and the second chamber having an outlet for the filtered treatment liquid, the method comprising the steps of:

conveying treatment liquid from the source through the first chamber;

recirculating during a recirculation mode, all treatment liquid from the outlet of the first chamber to the inlet of the first chamber so that all treatment liquid exiting the first chamber is fed-back through a feedback line into the first chamber;

adding to the recirculating treatment liquid additional treatment liquid from the source;

measuring a clogging level of the filter;

comparing the measured clogging level with a predetermined clogging threshold;

intermittently purging during a purge mode, the first chamber when the measured clogging level reaches the predetermined clogging threshold;

measuring a frequency of purges of the first chamber;

comparing the measured purge frequency with a purge frequency reference value; and increasing flow speed of treatment liquid through the first compartment when the measured purge frequency exceeds the purge frequency reference value.

2. The method of claim 1, further including the step of intermittently purging the feedback line during the step of intermittently purging the first chamber.

3. The method according to claim 1, wherein the step of measuring a clogging level of the filter comprises the substeps of:

measuring a transmembrane pressure of the filter; and comparing the measured transmembrane pressure with a reference transmembrane pressure.

4. The method according to claim 3, wherein the reference transmembrane pressure is measured each time the filter is set in operation.

5. The method according to claim 1, wherein during the step of recirculating a substantially constant pressure is maintained in the second chamber of the filter.

6. The method according to claim 1, wherein the step of measuring a clogging level of the filter comprises the substeps of:

measuring the speed of rotation of a pump used for recirculating the treatment liquid through the first chamber of the filter;

comparing the measured speed of rotation with a reference speed of rotation.

7. The method according to claim 6, wherein the reference speed of rotation is a speed measured each time the filter is set in operation.

8. A method for cleaning a filter having a first chamber and a second chamber separated by filtering membrane, the first chamber having an outlet and having an inlet connected to a treatment liquid source, and the second chamber having an outlet for the filtered treatment liquid, the method comprising the steps of:

conveying treatment liquid from the source through the first chamber;

monitoring treatment liquid flow upstream of the filter using a first flow monitoring element;

monitoring treatment liquid flow downstream of a permeate filter using a second flow monitoring element;

recirculating during a recirculation mode, all treatment liquid form the outlet of the first chamber to the inlet of the first chamber so that all treatment liquid exiting the first chamber is fed-back into the first chamber;

adding to the recirculating treatment liquid additional treatment liquid from the source;

measuring a clogging level of the filter;

comparing the measured clogging level with a predetermined clogging threshold;

intermittently purging during a purge mode, the first chamber when the measured clogging level reaches the predetermined clogging threshold; and calibrating the first and second flow monitoring elements during the ste of purging by bypassing the filter, and flow connecting the first flow monitoring element to the second flow monitoring element.

* * * * *

UNITED STATES PATENT AND TRADEMARK OFFICE
CERTIFICATE OF CORRECTION

PATENT NO. : 6,039,877
DATED : March 21, 2000
INVENTOR(S) : CHEVALLET et al., Jacques It is certified that error appears in the above-identified patent and that said Letters Patent is hereby corrected as shown below:

```
Claim 8, Col. 10, line 21, after "by" insert
    --a--;
        Col. 10, line 34, change "form"
to --from--;
        Col. 10, line 46, change "ste"
to --step- and after "filter" delete --,--.
```

Signed and Sealed this

Twenty-fourth Day of April, 2001

Attest:

NICHOLAS P. GODICI

Attesting Officer     Acting Director of the United States Patent and Trademark Office